(12) United States Patent
Nevelös et al.

(10) Patent No.: US 8,529,572 B2
(45) Date of Patent: Sep. 10, 2013

(54) HEAD CENTERING JIG FOR FEMORAL RESURFACING

(75) Inventors: James Nevelös, Chippenham (GB); Steven J. Krikler, Coventry (GB); Myron B. Stachniw, Galesburg, IL (US); Michael Bishay, Bath (GB)

(73) Assignee: Corin Limited, Gloucestershire (GB)

( * ) Notice: Subject to any disclaimer, the term of this patent is extended or adjusted under 35 U.S.C. 154(b) by 544 days.

(21) Appl. No.: 12/715,200

(22) Filed: Mar. 1, 2010

(65) Prior Publication Data

US 2010/0152742 A1    Jun. 17, 2010

Related U.S. Application Data

(62) Division of application No. 10/844,152, filed on May 12, 2004, now Pat. No. 7,695,476.

(30) Foreign Application Priority Data

May 12, 2003   (GB) .................................. 0310869.3

(51) Int. Cl.
*A61F 5/00* (2006.01)
(52) U.S. Cl.
USPC .......................................................... 606/87

(58) Field of Classification Search
USPC ........................ 606/86 R, 87–89, 96–98, 104
See application file for complete search history.

(56) References Cited

U.S. PATENT DOCUMENTS

| 4,896,663 A * | 1/1990 | Vandewalls ..................... 606/79 |
| 6,267,762 B1 * | 7/2001 | Millard et al. .................. 606/54 |

\* cited by examiner

*Primary Examiner* — Anu Ramana
(74) *Attorney, Agent, or Firm* — Leydig, Voit & Mayer, Ltd.

(57) ABSTRACT

There is described a jig for identifying a point on the femoral head which is in alignment with a central axis of the femoral neck. The jig comprises a first member which defines a plane and has means for at least partially receiving the femoral neck. The jig also comprises a guide member which is mounted apart from the first member and which defines an axis at right angles to the plane defined by the first member. The axis of the guide member intersects the plane at a point which is a predetermined distance away from the means receiving the femoral neck. In addition, the jig comprises an elongate alignment means which is mounted with respect to the first member and which is spaced apart from, but extends parallel to, the axis of the guide member. There is also described a kit for use in the resurfacing of the femoral head. The kit comprises at least one jig as previously described.

19 Claims, 12 Drawing Sheets

PRIOR ART

PRIOR ART

PRIOR ART

PRIOR ART

PRIOR ART

HEAD CENTERING JIG FOR FEMORAL RESURFACING

CROSS-REFERENCE TO RELATED APPLICATIONS

This patent application is a divisional of U.S. patent application Ser. No. 10/844,152, filed on May 12, 2004, now U.S. Pat. No. 7,695,476 which claims priority to United Kingdom Patent Application No. 0310869.3, which was filed on May 12, 2003.

FIELD OF THE INVENTION

The present invention relates to a head centering jig for use in the preparation of the femur in hip resurfacing procedures and to a kit comprising such a jig.

BACKGROUND OF THE INVENTION

Conventional Total Hip Replacement (THR) is a very successful procedure for the treatment of arthritis of the hip, a condition which causes considerable pain and loss of movement. As is well known, the hip is a ball and socket joint which allows the upper leg to move from side to side, back to front, and to rotate. The joint is made up of the head of the femur (the ball) which fits into the acetabulum (the socket). In a healthy hip, both the head of the femur and the acetabulum are covered with cartilage which provides a smooth surface allowing the joint to move freely.

The earliest Total Hip Replacement (THR) procedure, in 1938, involved an implant in which both surfaces were made from metal and was known as a metal-on-metal bearing. During the 1950's and early 1960's, a number of surgeons developed hip implants using this type of bearing, although many of these designs had a tendency to work loose early on as the techniques used to anchor them to the bone were not very successful. However, the implants that did not loosen early on have generally lasted well.

In the early 1960's, a British Surgeon, Sir John Charnley, developed a new type of Total Hip Replacement which is still in use today. This procedure, which is illustrated in FIG. 1, involves cutting the worn head off the femur and replacing it with a metal ball 10 and stem 12 in the shaft of the femur 14 and a plastic cup 16 in the pelvis 18. Both elements are typically anchored to the bone by "bone cement". This has become a very common surgical procedure with some 45,000 hip replacements being carried out in the UK every year.

The plastic used to form the cup 16 is inert and so is well tolerated by the body. Nevertheless, as the metal ball 10 rubs against the plastic cup 16, tiny particles of the plastic are worn away. This plastic debris causes an irritation. Furthermore, as the particles get between the bone and the artificial joint, this irritation causes surrounding bone to be absorbed by the body, leading to a loosening of the artificial joint. In older people, with a lower activity level, this may not happen for twenty or more years, but in younger, more active patients, this may happen much sooner.

To overcome these problems in younger, more active patients requiring hip replacement, a different type of implant was needed. In 1991 a procedure for metal-on-metal (MoM) resurfacing of the hip was proposed. This has two major differences from a conventional THR. The first is that both components are made from metal, typically Cobalt Chrome. By eliminating the plastic cup of a conventional THR, and making both parts of the bearing surface of metal, the resurfaced hip is expected to last much longer and therefore to be more suitable for higher demanding patients. The second difference is that the procedure is very bone conserving, since the head of the femur is simply reshaped and "resurfaced", rather than removed. Accordingly, should the device need replacing at some time in the future, this may provide better options for the surgeon at that time as a conventional THR can then be used.

A typical Resurfacing Hip is shown in FIG. 2 to comprise a femoral head component 20 and an acetabular cup 22. During the pre-operative planning stage, an X-ray of the hip is templated to assess the probable sizes for both the femoral head component 20 and acetabular cup 22. Alignment of the femoral head component 20 is also determined pre-operatively and is an important part of the templating procedure. The femoral head component 20 should be positioned in neutral or slight valgus alignment. Varus positioning should be avoided. Once the template has been satisfactorily positioned with respect to the X-ray, the distance is measured from the tip of the greater trochanter 24 to the point where the axis 26 of the femoral neck 32 crosses the lateral cortex of the femoral shaft 14. This pre-operative measurement is recorded as it indicates the position for subsequent insertion of a lateral positioning pin 28 of a head centering jig 30 (see FIG. 3 and related description below).

Initial preparation of the femur may be carried out to one size larger than that templated in order to ensure that there is sufficient clearance around the femoral neck 32 for the definitive implant. Further preparation to the templated size may then be carried out if it is evident that there is sufficient clearance around the neck 32 and that the integrity of the neck will not be compromised. Sufficient clearance may occasionally still remain to allow a smaller size to be used than was suggested by templating. In this case, further preparation to the smaller size may be carried out, ensuring the use of the most appropriate size of femoral components and minimizing the amount of bone removed from the acetabulum 34.

During hip resurfacing procedures it is common to prepare the femur first as this will debulk the femoral head 36 and facilitate access to the acetabulum 34. As part of this process the mid-lateral cortex of the femur is exposed and the position of the lateral positioning pin 28 is determined based on the pre-operative measurement taken from the X-ray. The lateral positioning pin 28 is then drilled into the mid-lateral cortex of the femur, initially using a lateral approach, but angling the pin towards the femoral head 36 once the outer cortex has been penetrated, as shown in FIG. 3.

Before proceeding with head centering, the size of the femoral head component 20 can be confirmed by placing an appropriate head template around the femoral neck 32. What is important to assess is that the appropriate clearance is available and that the femoral neck 32 will not be notched during preparation of the femur since this will result in a potential post-operative weakening of the hip.

In the past, once the size of the femoral head component 20 had been confirmed, a jig 30, such as that shown in FIG. 4, would be used to locate the centre of the femoral head 36. Since the femoral head 36 does not define a uniform sphere, what is important is to identify that point on the femoral head which coincides with the central axis 26 of the femoral neck 32.

As shown, the head centering jig 30 of the prior art comprises a hollow guide tube 38 having a proximal end 40 and a distal end 42. The guide tube 38 is supported by an arm 44 which locates at one end over the lateral positioning pin 28 and is provided at the other with a pawl 46 for selective engagement with a rack 48 provided on an outer surface of the guide tube. Thus, by the selective engagement and disengagement of the ratchet mechanism defined by the pawl 46 and rack 48 the guide tube 38 may be progressively advanced with respect to the arm 44. A locking screw 50 is provided to retain the guide tube 38 in fixed relation to the arm 44 once the desired relative position has been established.

A sleeve 52 is rotatably mounted to the guide tube 38 at a position intermediate the distal end 42 and the rack 48. As well as rotating, the sleeve 52 is also able to slide along the guide tube 38, thereby enabling the sleeve to be positioned at a range of distances from the distal end 42. A further locking screw 54 is provided to enable the sleeve 52 to be clamped longitudinally with respect to the guide tube 38 while still permitting a portion of the sleeve to rotate. To this rotating portion there is attached a projection 56 which extends in a direction perpendicular to a longitudinal axis of the guide tube 38. A stylus 58 is slidably mounted on the projection 56 to which it may be clamped in a selected one of a plurality of predetermined positions by means of a third locking screw 60. These predetermined positions correspond to different sizes of femoral head component 20 and are marked on the projection 56 as a series of graduations.

In order to identify the centre of the femoral head 36 the stylus 58 is set to the confirmed size of the femoral head component 20 and the third locking screw 60 is tightened to clamp the stylus with respect to the projection 56. The aim 44 of the head centering jig 30 is then located over the lateral positioning pin 28 and the guide tube 38 advanced towards the femoral head 36 in a controlled manner by means of the ratchet mechanism defined by the pawl 46 and rack 48. Centralization of the guide tube 38 is achieved by rotating the stylus 58 around the femoral neck 32. It is critical that a tip of the stylus 58 rotates freely around the femoral neck 32 at the head/neck junction without impingement. In this way it is possible to avoid subsequent notching of the femoral neck 32. In order to assess more easily whether the guide tube 38 is accurately centered with respect to the femoral head 36, the sleeve 52 may be slid along the guide tube to a point where the tip of the stylus 58 coincides with the junction of the femoral neck 32 and femoral head 36. The further locking screw 54 may then be tightened to retain the sleeve 52 in this longitudinal position with respect to the guide tube 38.

Once the guide tube 38 has been properly centered it can be locked into position by gently impacting into the femoral head 36 a plurality of circumferential teeth (not shown) provided on the distal end 42. A long pin 62 is then drilled through the guide tube 38 into the femoral head 36 before the head centering jig 30 is then disassembled and removed. If required, once the guide tube 38 has been disassembled from the arm 44, the guide tube and stylus 58 can be positioned over the long pin 62 to carry out a final check that the long pin is correctly positioned in relation to the femoral neck 32.

Thereafter, as shown in FIG. 5, a cannulated drill 64 is advanced over the long pin 62 as far as an appropriate line for the size of the femoral head component 20 being used. Both the cannulated drill 64 and the long pin 62 are then removed and a guide rod 66 inserted in their place.

As shown in FIG. 6, an appropriate size of head cutter 68 is advanced over the guide rod 66 as far as the junction between the femoral head 36 and femoral neck 32, ensuring that the femoral neck is not notched. During this process, the head template can be positioned around the femoral neck 32 to protect the neck and trochanter 24, while swabs can be used to prevent bone debris entering the soft tissue. If necessary, a larger size of head cutter 68 may be used for initial preparation of the femoral head 36 prior to final preparation with the definitive size in order to debulk the head.

Having removed the head cutter 68, the guide rod 66 is also then removed and a top head guide 70 placed over the prepared head surface and advanced to the head/neck junction. As shown in FIG. 7, a locking screw 72 is provided to hold the top head guide 70 in place while the top of the femoral head is resected. If necessary, a short pin (not shown) can be impacted through a hole in the top head guide 70 if additional security is required during the head resection. Following resection the guide rod 66 is reinserted and a top head cutter 74 advanced along the guide rod to create a flat surface perpendicular to the neck axis 26. As a result, the femoral head 36 acquires the shape shown in FIG. 8. An appropriate size of head chamfer cutter 76 is then used to create a bevel as shown in FIG. 9. Having thus shaped the femoral head 36, a corresponding size of head template 78 is used to check the prepared shape as shown in FIG. 10 and to make a mark on the head/neck junction to indicate how far the femoral head component 20 should be advanced if fully seated. Cement keyholes can be drilled into the femoral head 36 at this stage if required.

Having prepared the acetabulum 34 and fitted the acetabular cup 22, the femoral head component 20 is similarly implanted to the prepared femoral head 36. If a cemented head is used, low viscosity bone cement is poured into the femoral head component 20 up to a line at the top of a chamfer on the inside of the implant. The definitive component 20 is then placed onto the femoral head 36 and impacted into position using a head impactor 80 as shown in FIG. 11. Any excess bone cement may then be removed. Low viscosity cement is used in preference to high viscosity cement since high viscosity cement may prevent full seating of the femoral head component 20. However, cementless head components are also available and these are simply impacted into position using the head impactor 80.

With both components now fitted, the lateral positioning pin 28 is removed and the hip reduced while at the same time avoiding scratching the femoral head component 20 against the rim of the acetabular cup 22. A full check is then made to ensure that there is no impingement and that the range of movement and stability are satisfactory.

Thus, it can be seen that accurately determining the centre of the femoral head 36 is a critical step in a hip resurfacing procedure since it determines not only the position of the long pin 62 and the guide rod 66 but also the relative positions of all the cutters and guides that are subsequently used to shape the femur. There are, however, a number of problems with the prior art head centering jig shown in FIG. 3.

Firstly, the prior art jig 30 requires the use of a lateral positioning pin 28 which must be correctly positioned with respect to the femoral neck 32. This not only requires preoperative planning but also the intra-operative exposure of the mid-lateral cortex of the femur. Furthermore, having been inserted, it becomes necessary to remember to remove the lateral positioning pin 28 from the femoral cortex before the wound is closed. Although this might seem obvious, experience has taught that it is a sensible precaution to attach a chain 82 or other reminder to the lateral positioning pin 28 to ensure that its removal is not overlooked.

Another problem with the prior art head centering jig 30 is that it is bulky since the arm 44 must extend from the lateral positioning pin 28 at the mid-lateral femoral cortex to the femoral head 36 while still allowing the stylus 58 to rotate about the guide tube 38.

The prior art head centering jig 30 also requires the use of two hands, one to hold the guide tube 38 and the other to rotate the stylus 58.

It would therefore be advantageous to provide an improved head centering jig which was less bulky and could be operated with only one hand. It would also be advantageous if the use of the head centering jig no longer necessitated exposure of the mid-lateral cortex of the femur.

SUMMARY OF THE INVENTION

According to a first aspect of the present invention there is provided a jig for identifying a point on the femoral head in alignment with a central axis of the femoral neck, the jig comprising a first member defining a plane and having means for at least partially receiving the femoral neck; a guide member mounted in spaced relation with respect to the first member and defining an axis at right-angles to the plane defined by the first member, the axis intersecting the plane at a point a predetermined distance from said means for at least partially receiving the femoral neck; and elongate alignment means mounted with respect to the first member, the alignment means being spaced from and extending parallel to the axis defined by the guide member.

Advantageously, the guide member may comprise a hollow tube and the axis defined by the guide member may comprise a central axis of the tube. This provides for accurate positioning of the drill required to drill the long pin into the femoral head. Alternatively, the guide member may comprise a channel member. This provides the advantage of not having to disassemble the jig prior to its removal once the long pin has been drilled into the femoral head.

Advantageously the guide member may be mounted with respect to the first member so as to selectively detachable therefrom. This facilitates the disassembly of the jig. Preferably the guide member may be separable from the first member in a direction parallel to the axis defined by the guide member. This facilitates the removal of the guide member over the long pin once the long pin has been drilled into the femoral head.

Advantageously the first member may comprise a handle. This facilitates the ease with which the jig may be manipulated by a surgeon. Preferably the means for at least partially receiving the femoral neck may be adapted to so receive the femoral neck when the means is offered up to the femoral neck in a first direction, the handle extending in a direction parallel to the first direction. This increases the ease with which the jig may be used. Preferably the elongate alignment means may be spaced from the axis defined by the guide member in a second direction, the second direction being orthogonal to the direction in which the handle extends. Likewise, when the means for at least partially receiving the femoral neck is adapted to so receive the femoral neck when the means is offered up to the femoral neck in a first direction, the elongate alignment means may be spaced from the axis defined by the guide member in a second direction, the second direction being orthogonal to the first direction. This facilitates the alignment of the guide member with the central axis of the femoral neck.

Advantageously the elongate alignment means may be adapted to be mounted with respect to the first member in a selected one of two positions, the two positions being spaced on opposite sides of the axis defined by the guide member. This enables the jig to be adapted depending on whether the surgeon is either left handed or right handed or whether the femoral head that is being reshaped is the patient's left or right. Preferably the two positions may be mirror images of each other.

Advantageously the elongate alignment means may extend through the plane defined by the first member. This further facilitates the alignment of the guide member with the central axis of the femoral neck.

Advantageously the elongate alignment means may be adapted to be mounted with respect to the first member in a selected one of a plurality of positions spaced at different distances from the axis defined by the guide member. This enables the jig to accommodate femoral heads of different dimensions and enables the elongate alignment means to be spaced at different distances from the femoral neck in accordance with the preference of the surgeon.

Advantageously the elongate alignment means may comprise at least one rod. Where the elongate alignment means comprises first and second rods mounted with respect to the first member and extending parallel to and spaced from the axis defined by the guide member, the first rod may be spaced from the axis in a direction orthogonal to that in which the second rod is spaced from the axis. This facilitates the alignment of the guide member with the central axis of the femoral neck by providing a means for obtaining simultaneous alignment in two orthogonal planes. Where the elongate alignment means comprises first and second rods and where the first member comprises a handle, one of the first and second rods may extend along an axis that intersects the handle.

Advantageously, the first member may comprise means adapted to substantially encircle the femoral neck. This enables the first member to be more accurately positioned with respect to the femoral neck. Preferably the means for substantially encircling the femoral neck may comprise a first part hingedly mounted at a first end with respect to a second part and moveable between an open position in which an opposite end remote from the hinge is separated from the second part by a distance sufficient to receive the femoral neck and a closed position in which the parts define a wall adapted to substantially surround the femoral neck. Preferably the wall defined by the first and second parts in the closed position subtends an angle of 270° or more. Preferably, in the closed position, the arc subtended by that part of the wall defined by the first part is substantially the same as the arc subtended by that part of the wall defined by the second part.

Preferably, in the closed position, the first and second parts may define a circular aperture for the receipt of the femoral neck. Under such circumstances the axis defined by the guide member may intersect the plane defined by the first member at the centre of the circular aperture defined by the first and second parts. This ensures that when the elongate alignment means is aligned with the femoral neck, the axis defined by the guide member coincides with the central axis of the femoral neck.

Advantageously means may be provided to releasably retain the first and second parts in the closed position. This provides the advantage of preventing the first member from becoming accidentally dislodged from the femoral neck. Preferably the first and second parts are each provided with a respective aperture, the aperture of the first part being adapted to be aligned with the aperture of the second part when the first and second parts are in the closed position, the mutually aligned apertures being adapted to receive the means for releasably retaining the first and second parts in the closed position. Preferably the guide member comprises the means adapted to be received within the mutually aligned apertures to releasably retain the first and second parts in the closed position.

According to a second aspect of the present invention there is provided a kit for use in the resurfacing of the femoral head, the kit comprising at least one jig as previously described.

Advantageously, the kit may comprise a plurality of jigs, each jig being as previously described and differing from each other in terms of the dimensions of the means for at least partially receiving the femoral neck and/or the predetermined distance from said means at which the axis defined by the guide member intersects the plane defined by the first member. This provides the advantage of enabling the kit to accommodate the range of femur sizes present in the population.

According to a third aspect of the present invention there is provided a method of identifying a point on the femoral head in alignment with a central axis of the femoral neck, the method comprising the steps of: providing a jig comprising a first member defining a plane and having means for at least partially receiving the femoral neck, a guide member mounted in spaced relation with respect to the first member and defining an axis at right-angles to the plane defined by the first member, the axis intersecting the plane at a point a predetermined distance from said means for at least partially receiving the femoral neck, and elongate alignment means mounted with respect to the first member, the alignment means being spaced from and extending parallel to the axis defined by the guide member, exposing the femoral head and neck; offering up the first member to the femoral neck so that the femoral neck is at least partially received by said means for at least partially receiving the femoral neck; aligning the elongate alignment means with a central axis of the femoral neck; and identifying a point at which the axis defined by the guide member intersects the femoral head as the point on the femoral head in alignment with the central axis of the femoral neck.

Preferably the mid-lateral cortex of the femur is not exposed.

Advantageously the first member is offered up to the femoral neck and the elongate alignment means is aligned using only one hand. Preferably the first member is offered up to the femoral neck in a lateral approach.

Preferably the step of offering up the first member to the femoral neck comprises substantially encircling the femoral neck.

Advantageously the step of aligning the elongate alignment means comprises aligning the elongate alignment means with a central axis of the femoral neck when viewed from two orthogonal directions.

Preferably the method further comprises the step of drilling along the axis defined by the guide member and into the femoral head. More preferably the method further comprises the step of disassembling the jig prior to removal from the femoral neck.

Advantageously the jig is provided as part of a kit comprising a plurality of jigs, each jig differing dimensionally from each other jig, the method further comprising the step of selecting the appropriate jig for the size of femoral head to be surveyed.

DETAILED DESCRIPTION OF EMBODIMENTS

Figure 1:
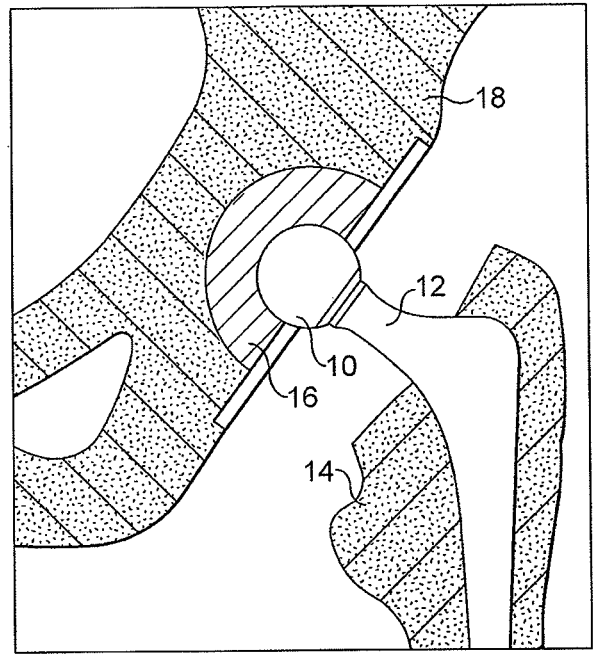
FIG. 1 is a fragmentary frontal view of a hip replacement according to a procedure of the prior art.
Figure 2:
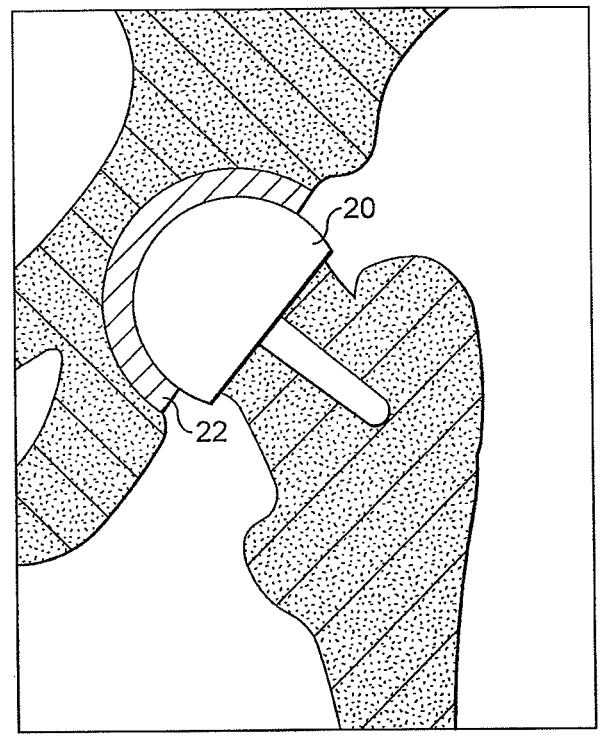
FIG. 2 is a fragmentary frontal view of a hip replacement according to a procedure of the prior art.
Figure 3:
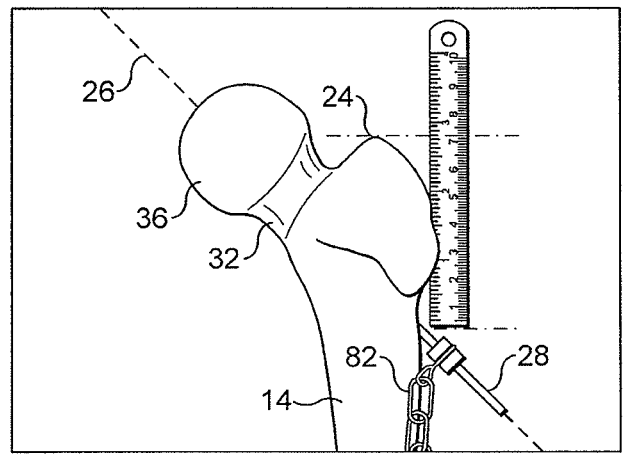
FIGS. 3-11 are fragmentary frontal views of hip replacement procedures and tools of the prior art.
Figure 4:
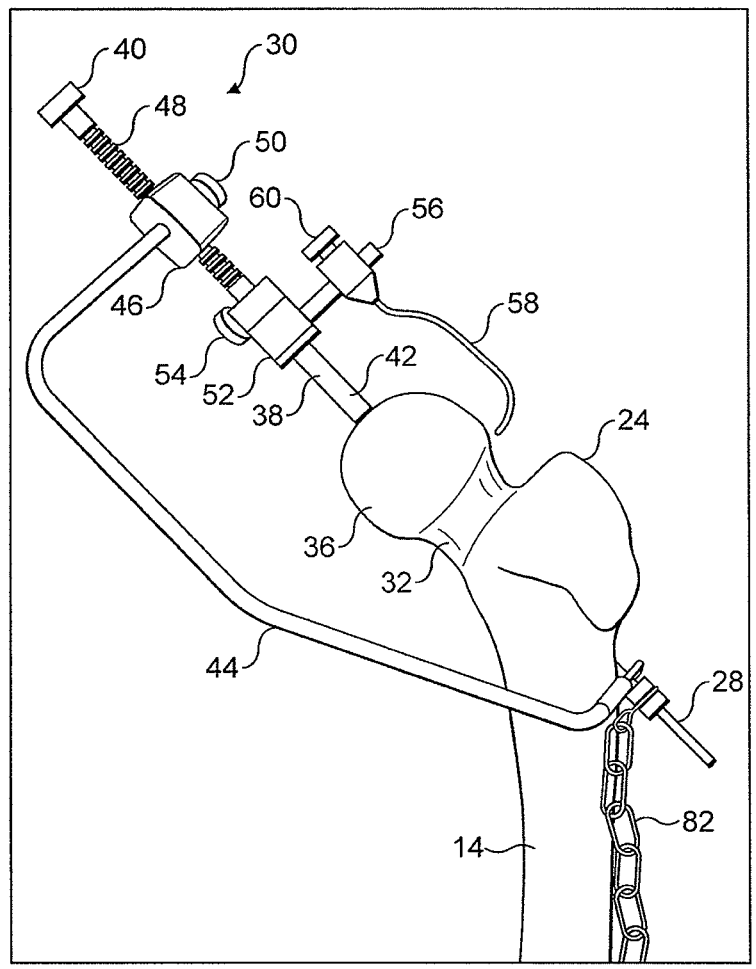
Figure 5:
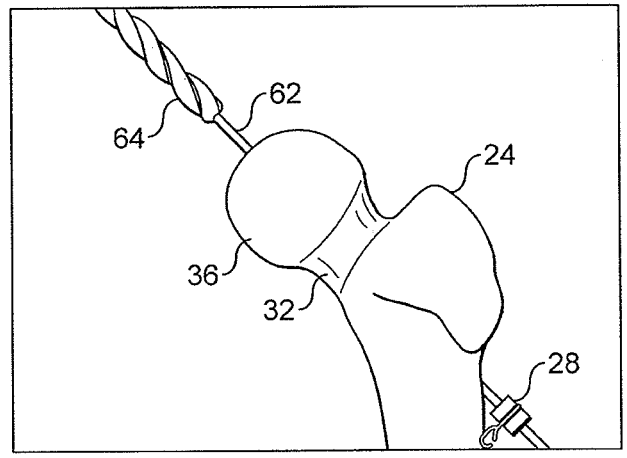
Figure 6:
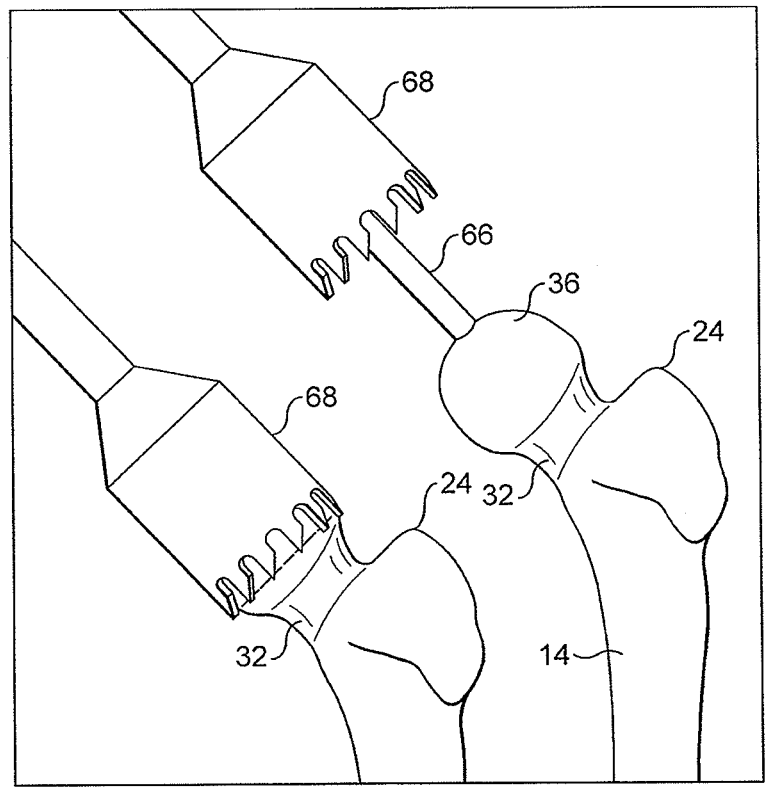
Figure 7:
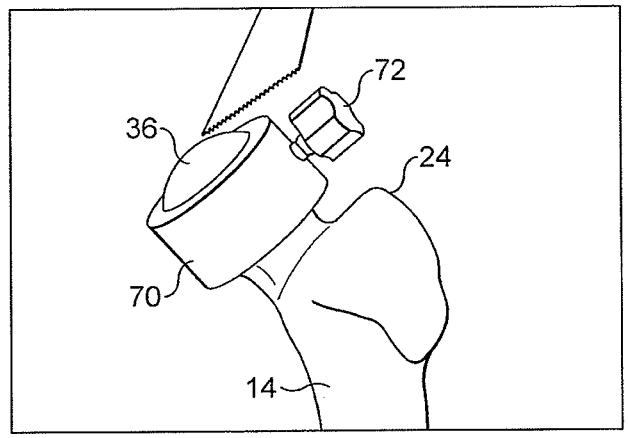
Figure 8:
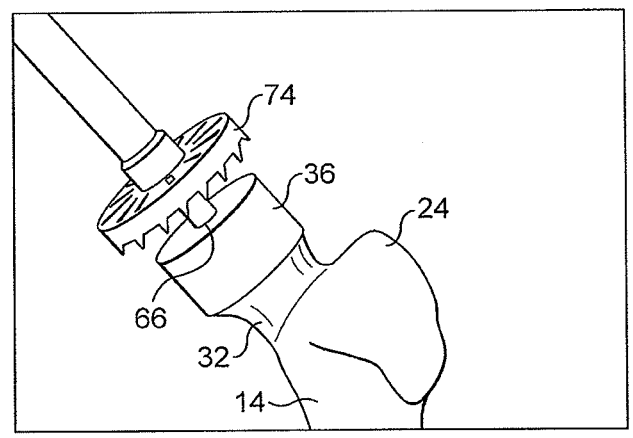
Figure 9:
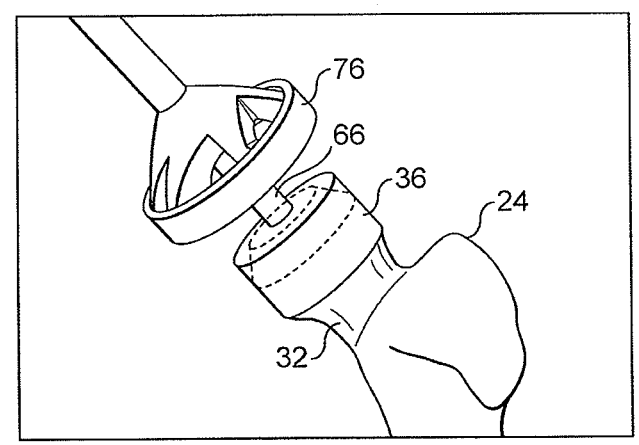
Figure 10:
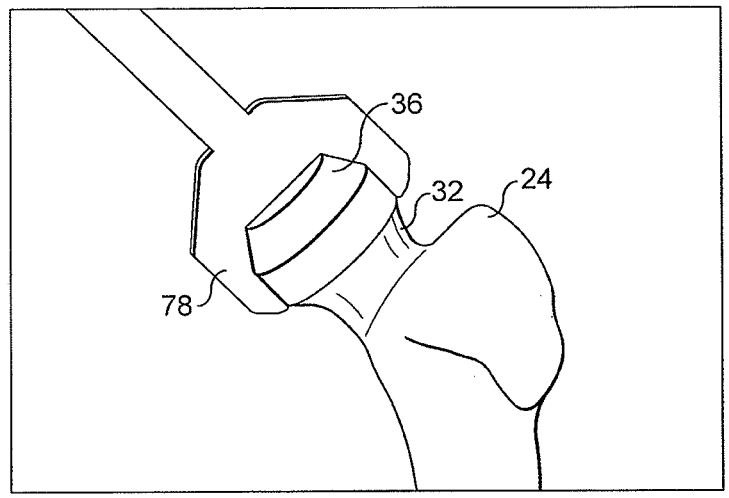
Figure 11:
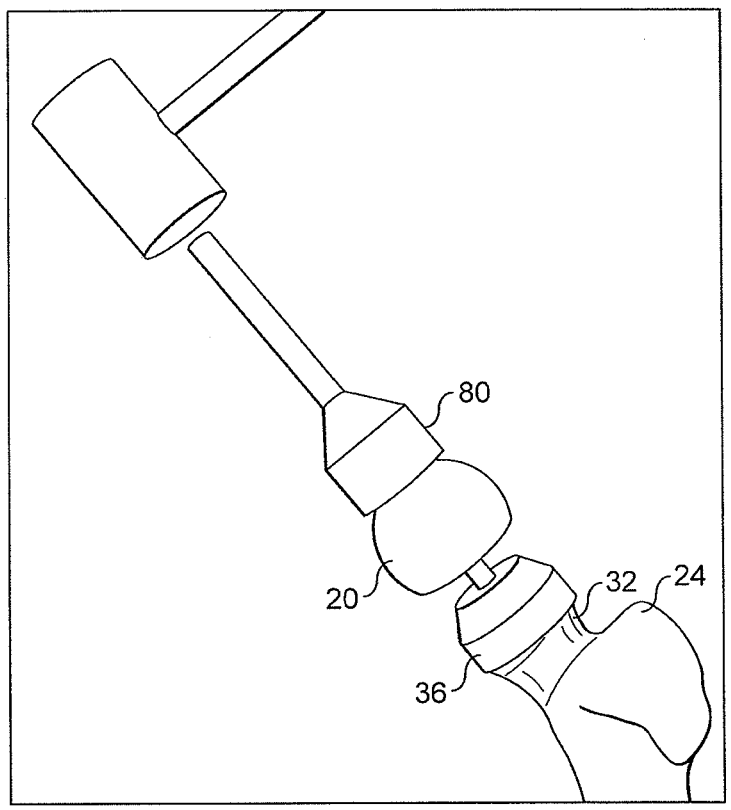

Referring to FIGS. 12 to 16 there is shown a head centering jig 100 comprising a substantially planar locating tool 102. In the embodiment, shown the locating tool 102 has a spanner-like form and is symmetrical about a longitudinal axis 103. The locating tool 102 comprises an elongate handle 104 having a rounded proximal end 106. At a distal end, the elongate handle 104 merges with a planar head portion 108. The head portion 108 is recessed at an edge opposite where the head portion merges with the handle 104 so as to define a mouth 112 having a pair of mutually spaced jaws 110 which extend away from the handle on either side of the longitudinal axis 103. In order to minimize the trauma caused in using the head centering jig 100, the head portion 108 is provided with an external profile devoid of sharp angles. Indeed, in some preferred embodiments, the external profile of the head portion 108 may be smoothly curved. By contrast, the mouth 112 is defined by a pair of confronting surfaces 105 and 107 which extend parallel to and are equally spaced from the longitudinal axis 103 and an orthogonal surface 109 which extends perpendicularly to the longitudinal axis and which, in some embodiments, may serve to join the confronting surfaces 105 and 107. In other embodiments, such as that illustrated, the orthogonal surface 109 is joined to the confronting surfaces 105 and 107 via respective angled surfaces 111 and 113 so that all of the surfaces defining the mouth 112 subtend an oblique angle with the surface or surfaces adjacent to them. In this way the mouth 112 has an internal profile which, in plan view, approximates to a U-shape. In some embodiments this internal profile may be made smoother still such that the confronting surfaces 105 and 107 are joined by an arcuate or semicircular surface (not shown).

A retaining member 114 is releasably mounted to the locating tool 102 and is carried on an upper surface of the handle 104 adjacent the distal end where the handle merges with the head portion 108. To this end, the handle 104 is provided with three apertures 115, 117 and 119 which are spaced in the longitudinal direction along the longitudinal axis 103. In use the central of these three apertures 117 communicates with a threaded bore 121 provided in an undersurface of the retaining member 114. As a result, a complimentary threaded locking screw 116 may pass through the central aperture 117 to engage the threads of the blind bore 121 and in so doing releasably secure the retaining member 114 with respect to the locating tool 102. In order to facilitate the alignment of the retaining member 114 with respect to the locking tool 102, the same undersurface having the blind bore 121 is also provided with two projecting studs 118 and 120. When the retaining member 114 is correctly aligned with respect to the locking tool 102, these projecting studs 118 and 120 are received within the outer pair of the apertures 115 and 119 provided in the handle 104.

As can be seen, the retaining member 114 comprises an elongate foot 122 which is releasably attached to the locating tool 102 by means of the locking screw 116 and extends in a direction coincident with the longitudinal axis 103, an upstanding member 124 which merges with the foot 122 and projects upwardly from the handle 104 perpendicular to the plane defined by the locating tool 102, and an arm 126 which merges with the upstanding member 124 at an end remote from the foot 122 and extends in a plane parallel to and spaced from that defined by the locating tool 102. The arm 126 extends in a direction parallel to the longitudinal axis 103 and, at an end remote from the upstanding member 124, terminates in an arcuate surface. This enables the arm 126 to abut, and in some embodiments be welded, brazed or otherwise joined to the cylindrical outer surface of a hollow guide tube 128.

In those embodiments in which the guide tube 128 is not joined to the arm 126, the guide tube 128 may nonetheless be secured to the retaining member 114 by means of a collar 130 which surrounds the guide tube 128 and retains the guide tube in a friction fit and is itself attached to the arm 126 by means of a locking screw 132. Thus, the collar 130, as well as having a central aperture 131 for receipt of the guide tube 128, is provided with a first radial projection 134 having a through bore 133 located at an end remote from the collar. When the guide tube 128 abuts the arcuate end surface of the arm 126 this through bore 133 communicates with a threaded bore 135 provided in the arm such that the complimentary threaded locking screw 132 may pass through the first radial projection and into threaded engagement with the bore provided in the arm 126.

With the guide tube 128 joined or secured in this position, a central axis 136 of the guide tube intersects the plane defined by the locking tool 102 at a location along the longitudinal axis 103 and within the mouth 112 a predetermined distance from the orthogonal surface 109. In those embodiments in which the internal profile of the mouth 112 approximates to a U-shape, this predetermined distance may be approximately equal to half the distance separating the confronting surfaces 105 and 107. Likewise, in those embodiments in which the confronting surfaces 105 and 107 are joined by a semicircular surface, the central axis 136 of the guide tube 128 may intersect the plane defined by the locating tool 102 at the centre of the circle defined by that semicircular surface. In those embodiments in which the confronting surfaces 105 and 107 are joined by an arcuate surface, the point of intersection may coincide with the centre of curvature of the arcuate surface.

In addition to the first radial projection 134, the collar 130 is also provided with a second radial projection 138. This second radial projection 138 is longer than the first and extends at right-angles to it. By definition therefore, the second radial projection 138 also extends at right-angles to the arm 126. A plurality of apertures 140 are provided at intervals along the centre line of the second radial projection and are sized so as to slidably receive one end 142 of a first alignment rod 144. As can be seen, the alignment rod 144 is of circular cross-section and has a diameter that is stepped at a location intermediate the ends of the rod such that, at one end 142, the alignment rod has a diameter capable of being received through a selected one of the apertures 140 and, at the other end 146, has a diameter which is not so capable. As a result, an annular shoulder 145 is formed at the location where the diameter of the alignment rod increases and it is this shoulder which abuts an upper surface of the second radial projection 138 and prevents the alignment rod 144 from passing completely through the selected aperture 140.

Although not strictly necessary, a second alignment rod 148, of similar construction to the first, may be arranged to pass through a selected one of a plurality of mutually aligned apertures 150 provided in the foot 122 and arm 126 of the retaining member 114 and in the handle 104 of the locating tool 102. As will be readily understood, both alignment rods 144 and 148 extend parallel to the central axis 136 of the guide tube 128 and perpendicular to the plane defined by the locating tool 102. Furthermore, in the same way that the first alignment rod 144 may be spaced from the axis 136 at different distances depending on the aperture 140 through which the alignment rod is received, so too may the second alignment rod 148 by appropriate selection of the mutually aligned apertures 150.

One of the advantages of the head centering jig 100 shown in FIGS. 12 to 16 is that, unlike the jig of the prior art, it does not require the provision of a lateral positioning pin. As a result the mid-lateral cortex of the femur need not be exposed during the Hip Resurfacing procedure and there is no risk of a positioning pin being left behind once the wound is closed. Instead, the only parts of the femur that need be exposed are the femoral head and femoral neck. Accordingly, once this has been achieved, in order to identify the point on the femoral head in alignment with the central axis of the femoral neck the surgeon simply selects a head centering jig appropriate to the patient. In order to accommodate the range of femur sizes present in the population it will be necessary to provide a range of jigs which differ in terms of the dimensions of the mouth 112. The length of the arm 126 would also vary from jig to jig in order to maintain the relationship between the central axis 136 of the guide tube 128 and its point of intersection with the plane defined by the locating tool 102. Nevertheless, this range of jigs may be made so that each jig 100 corresponds to a respective one of the standard sizes of femoral head component.

The head centering jig 100 is offered up to the femur using a lateral approach. In so doing, by making use of the elongate handle 104 the surgeon is able to grip the jig using only one hand. This represents another significant advantage over the head centering jigs of the prior art. The locating tool 102 is positioned so that the femoral neck is received between the mutually spaced jaws 110 and abutting the orthogonal surface 109. With the femoral neck thus received within the mouth 112, the plane defined by the locating tool 102 is tilted by raising and lowering the handle 104 until such time as the first alignment rod 144 is aligned parallel to the central axis of the femoral neck when viewed anteriorly. Assuming that the appropriately sized jig has been selected and that the femoral neck is a close fit between the jaws 110 of the locating tool 102, the central axis 136 of the guide tube 128 will lie within a plane parallel to the coronal plane. By then aligning the first alignment rod 144, the central axis 136 is brought into coincidence with the central axis of the femoral neck. Thus, using his free hand, the surgeon may then drill the long pin through the guide tube 128 and into the femoral head.

If additional alignment is required and if the head centering jig 100 is provided with a second alignment rod 148 then, once the first alignment rod 144 has been aligned with the central axis of the femoral neck when viewed anteriorly, the second alignment rod 148 may be aligned with a central axis of the femoral neck when viewed laterally. This alignment of the second alignment rod 148 ensures that the central axis 136 of the guide tube 128 lies within a plane parallel to the coronal plane notwithstanding any small amount of play between the femoral neck and the jaws 110 of the locating tool 102 and, if performed simultaneously with the similar alignment of the first alignment rod 144, ensures that the central axis 136 coincides with the central axis of the femoral neck. However, as stated previously, assuming that the appropriate jig 100 has been selected and the jaws 110 are appropriately spaced, this secondary alignment should not be necessary. Even if it does prove necessary, the surgeon may choose to align the upstanding member 124 with the central axis of the femoral neck to the same effect rather than employ a second alignment rod 148.

Once the long pin has been drilled into the femoral head the head centering jig 100 is disassembled and removed. In order to achieve this, the locking screw 116 is unscrewed from the blind bore 121 thereby enabling the retaining member 114 to be separated from the locating tool 102. The retaining member 114, the guide tube 128 and the first alignment rod 144 are then removed over the long pin in a direction parallel to the central axis 136. If a second alignment rod 148 is provided then this too is removed from the locking tool 102 in a direction parallel to the central axis 136. By contrast, the locking tool 102 is removed laterally in a direction perpendicular to the long pin. With the head centering jig 100 removed from the wound, the remainder of the Hip Resurfacing procedure may be performed in the manner previously described with a cannulated drill being advanced over the long pin as the next step in the reshaping of the femoral head.

Although the head centering jig 100 has been described as comprising a hollow guide tube 128 defining a central axis 136, it will be apparent that in certain embodiments the hollow guide tube may be replaced by a channel member of U-shaped or V-shaped cross-section sized to receive a drill for drilling the long pin into the femoral head and capable of uniquely defining a drill axis perpendicular to the plane of the locating tool 102. The advantage of such an embodiment is that the channel member does not surround the drill axis so that once the long pin has been drilled into the femoral head, the channel member, retaining member and locating tool may be removed from the femur in a single operation and without requiring the disassembly of the head centering jig.

Figure 12:
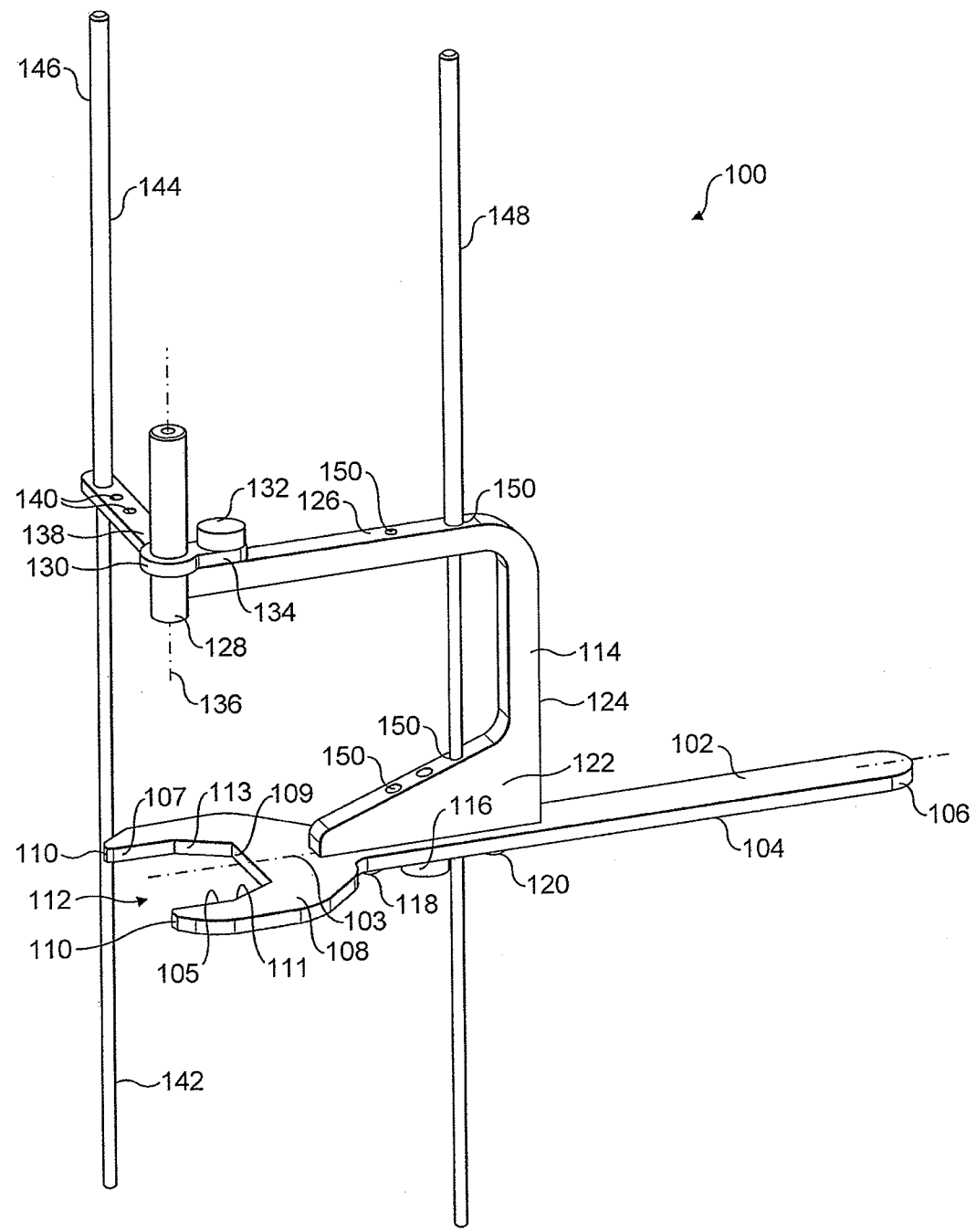
FIG. 12 is a perspective view of a head centering jig in accordance with a first embodiment of the present invention.
Figure 13:
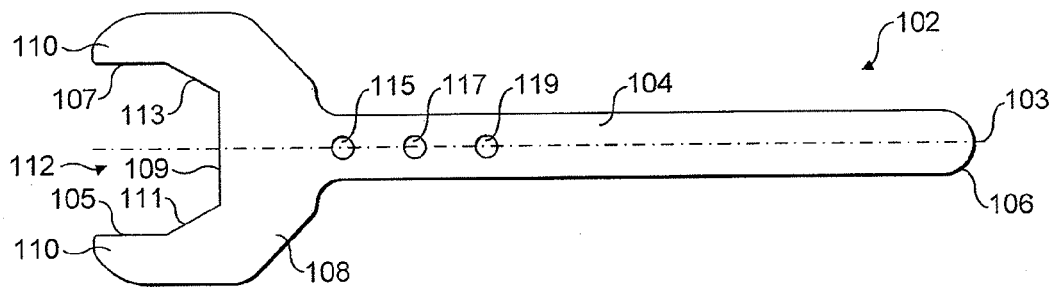
FIG. 13 is a plan view of a locating tool used in the first embodiment of the present invention.
Figure 14:
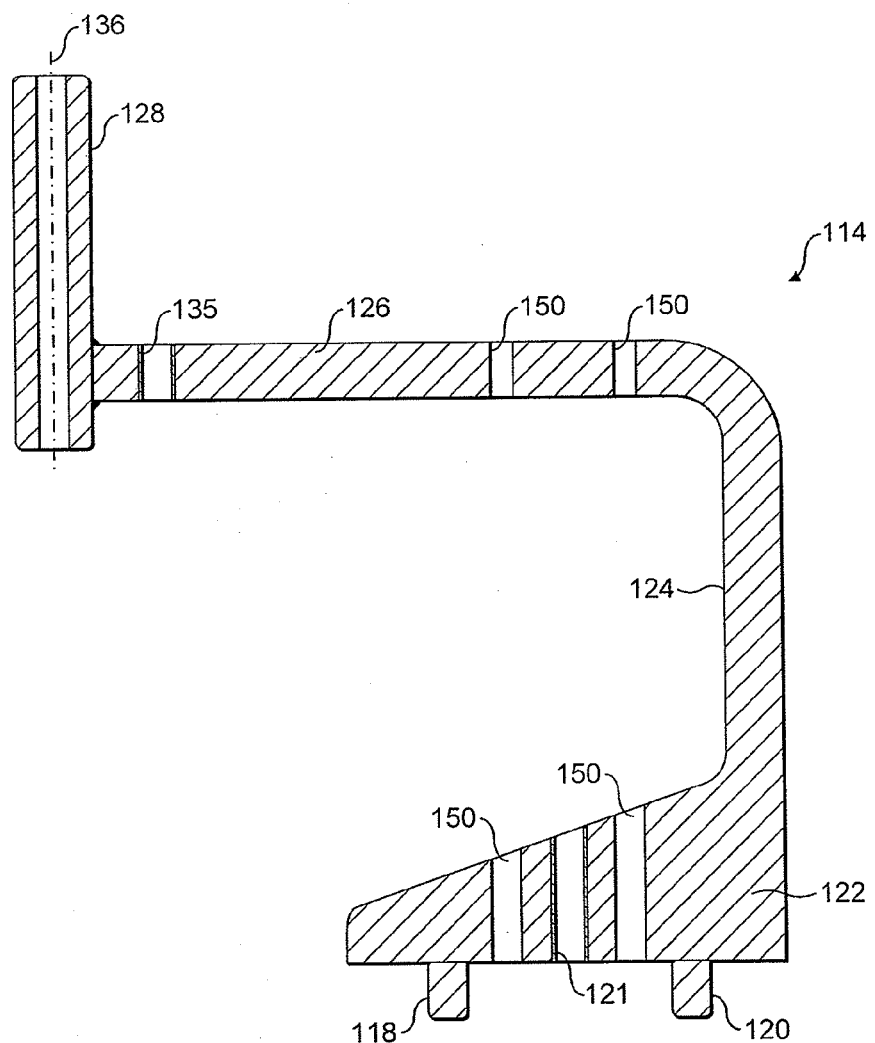
FIG. 14 is a cross-sectional view of a retaining member used in a first embodiment of the present invention.
Figure 15:
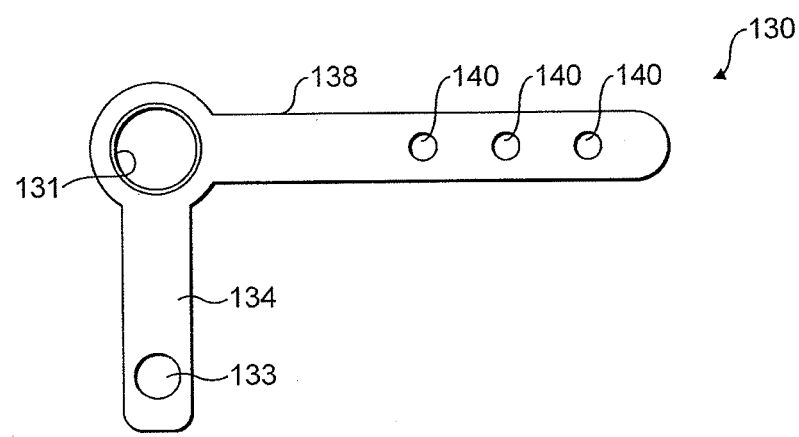
FIG. 15 is a plan view of a collar used in a first embodiment of the present invention.
Figure 16:
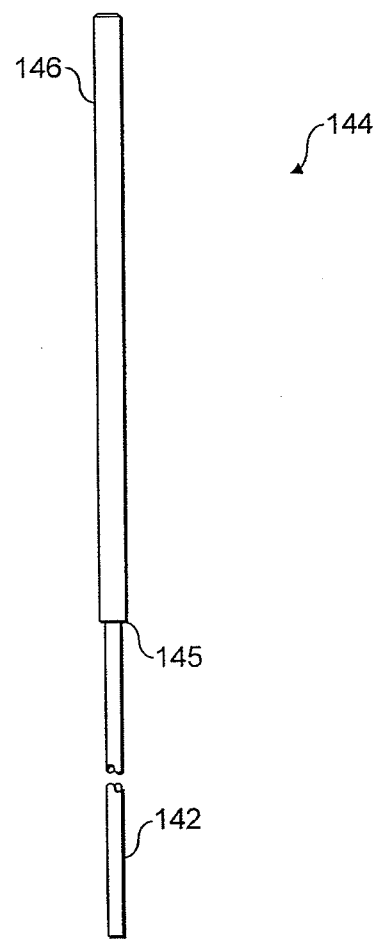
FIG. 16 is a side view of an alignment rod used in a first embodiment of the present invention.

Another advantage of the present head centering jig 100 is that the first alignment rod 144 may be located with respect to the guide tube 128 on either side of the retaining member 114. This may be useful depending on the handedness of the surgeon or whether the femoral head that is being reshaped is the patient's left or right. Thus, for example, by unscrewing locking screw 132 from threaded bore 135, the collar 130 may be removed from the arm 126 and inverted before being reassembled to the retaining member 114. In this way, the second radial projection 138, instead of projecting to the right when viewed along the aim 126 in the direction of the guide tube 128, as shown in FIG. 12, projects to the left.

Figure 17:
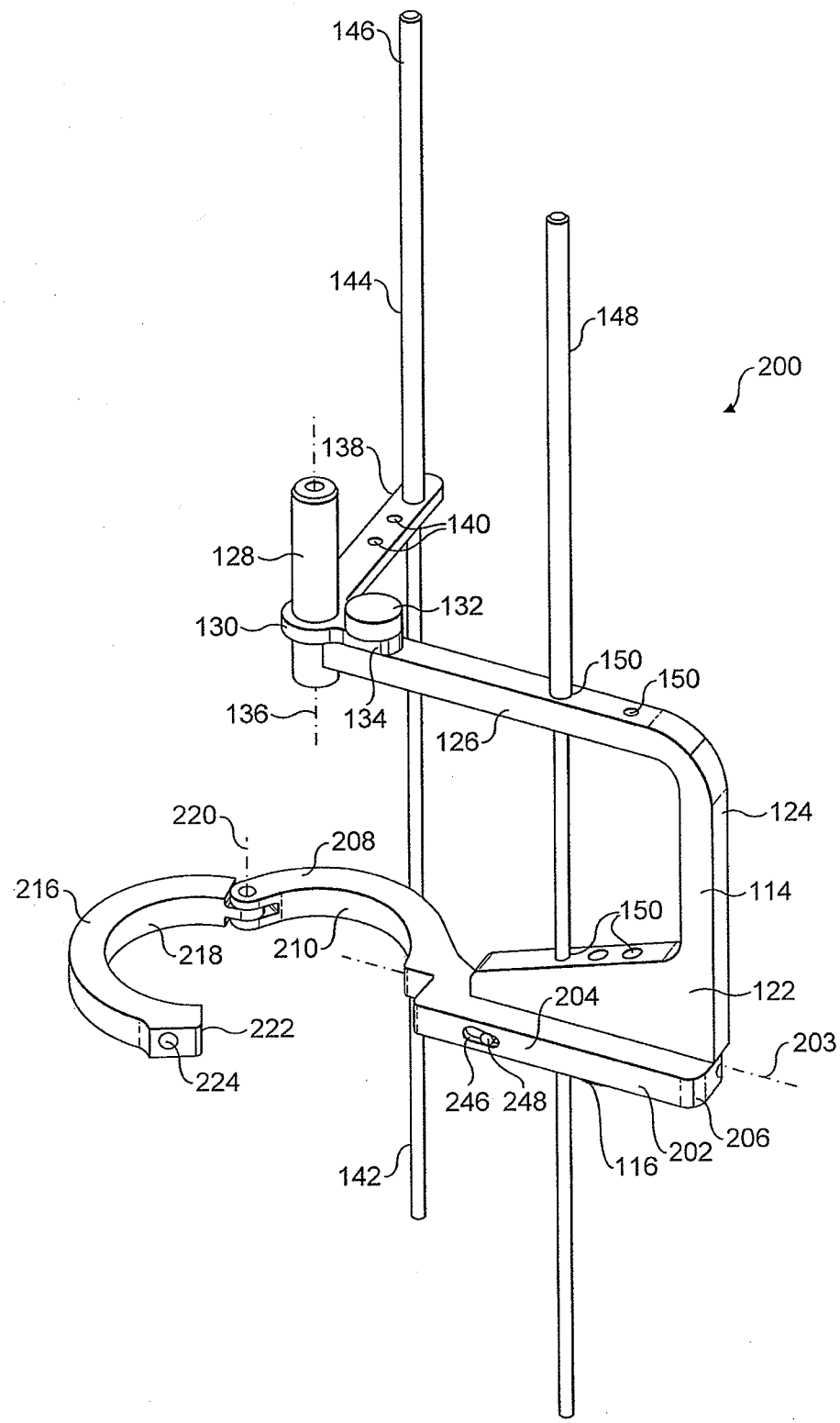
FIG. 17 is a perspective view of a head centering jig in accordance with a second embodiment of the present invention.
Figure 18:
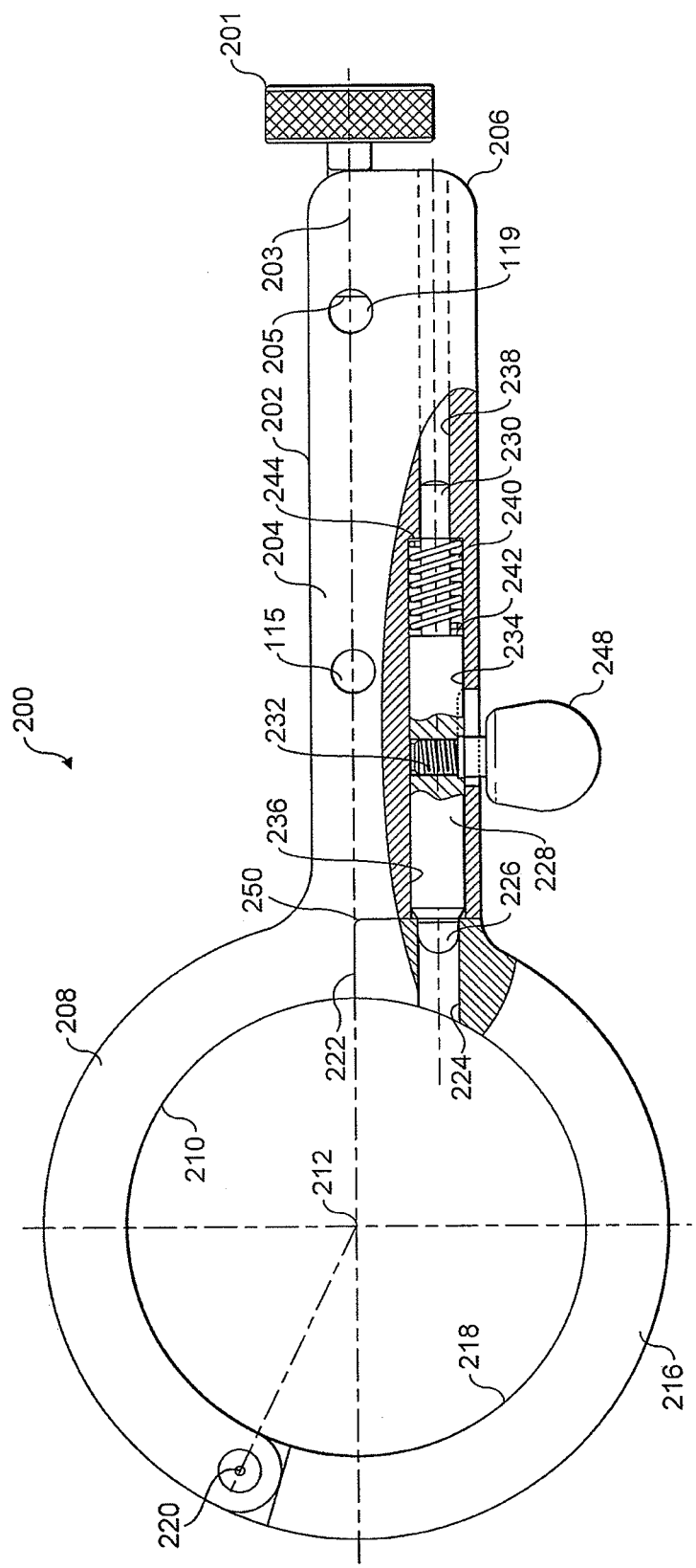
FIG. 18 is a plan view, partially in cross-section, of a locating tool used in a second embodiment of the present invention.

A head centering jig 200 in accordance with a second embodiment of the present invention is shown in FIGS. 17 and 18. Many of the features of the second embodiment, including the retaining member 114, the guide tube 128 and the two alignment rods 144 and 148 are similar to those described in relation to the first embodiment and so will not be further described in relation to the second embodiment in which they are denoted by the same reference numerals. Nevertheless, the locating tool 202 of the second embodiment does differ from that of the first embodiment although, like the first embodiment, it comprises an elongate handle 204 having a rounded proximal end 206.

Although the retaining member 114 may be secured to the handle 204 by means of a locating screw 116 in the same manner as has been described with reference to the first embodiment and, indeed, as illustrated in FIG. 17, the retaining member 114 may equally be attached to the handle 204 by means of the fixation mechanism illustrated in FIG. 18. In this arrangement the handle 204 is again provided with a pair of apertures 115 and 119 for the receipt of the projecting studs 118 and 120 provided on an undersurface of the retaining member 114. However, whereas in the first embodiment the retaining member 114 is releasably secured to the locating tool 102 by means of a threaded locking screw 116 passing through the handle 104 in a direction perpendicular to the plane defined by the locating tool 102, in the embodiment shown in FIG. 18 a locking screw 201 passes through a threaded aperture located within the plane of the handle 204 and extending along an axis 203 passing through the centers of the apertures 115 and 119. Indeed, the threaded aperture communicates with aperture 119 and, as a result, the locking screw 201 may be tightened so that an end of the locking screw 205 bears against the projecting stud 120 thereby releasably securing the retaining member 114 with respect to the locating tool 202.

At a distal end, the handle 204 merges with one end of a first arcuate member 208 which defines an arcuate surface 210 having a centre of curvature 212 which lies on the axis 203. A second arcuate member 216 is hingedly connected to the first arcuate member 208 at an end remote from the handle 204 and defines an arcuate surface 218 having the same centre and radius of curvature as the arcuate surface 210. Indeed, between them, the two arcuate surfaces 210 and 218 subtend a combined arc of 360° and it is at this centre of curvature 212 that the central axis 136 of the guide tube 128 intersects the plane defined by the locating tool 202.

The second arcuate member 216 is hinged with respect to the first arcuate member 208 about an axis 220 that extends perpendicular to the plane defined by the locating tool 202 such that the second arcuate member is moveable between an open position, shown in FIG. 17, and a closed position shown in FIG. 18. In the open position an end 222 of the second arcuate member 216 remote from the hinge axis 220 is spaced sufficiently far from the handle 204 to permit the receipt of the femoral neck. By contrast, in the closed position, the end 222 of the second arcuate member 216 abuts the handle 204 and the two arcuate surfaces 210 and 218 define a closed circle. As with the head centering jig of the first embodiment, in order to accommodate the range of femur sizes present in the population, it will be necessary, in accordance with the second embodiment, to provide a range of locating tools 202 which differ in terms of the diameter of the circle defined by the arcuate surfaces 210 and 218 in this closed position. The length of the arm 126 would also need to vary from jig to jig in order to maintain the relationship between the central axis 136 of the guide tube 128 and its point of intersection with the plane defined by the locating tool 202.

In order to retain the second arcuate member 216 in the closed position the member is provided adjacent the end 222 with a bore 224 sized to receive a head 226 of a locking pin 228. The body of the locking pin 228 is substantially cylindrical and terminates at an end remote from the head 226 in an axial projection 230. Approximately mid-way between the head 226 and the axial projection 230 the locking pin 228 is provided with a threaded bore 232 that extends perpendicularly to a longitudinal axis of the locking pin.

The locking pin 228 is received within a stepped bore 234 provided in the handle 204 which communicates with the bore 224 provided in the second arcuate member 216 when the second arcuate member is in the closed position. Furthermore, the stepped bore 234 extends in a direction parallel to axis 203 and comprises a first region 236 having a diameter sufficient to receive the body of the locking pin 228 and a second region 238 of reduced diameter remote from the bore 224 sufficient only to receive the axial projection 230.

In order to assemble the locking pin 228, a helical spring or other resilient member 240 is positioned over the axial projection 230 and the spring and locking pin 228 are inserted into the stepped bore 234 so that an end of the axial projection protruding from the spring is received within the second region 238. In this way the spring is held captive between an end of the body of the locking pin 242 and an annular shoulder 244 defined at the intersection of the first and second regions 236 and 238 of the stepped bore 234. A slot 246 is provided in a side wall of the handle 204 so as to communicate with the threaded bore 232. A threaded stud 248 may then pass through the slot 246 and into threaded engagement with the bore 232. Thus, whilst the locking pin 228 is biased by the spring 240 in a first direction so as to cause the head 226 to project out of the stepped bore 234 and be received within the communicating bore 224, movement of the stud 248 in the opposite direction compresses the spring 240 and allows the head 226 to be withdrawn from engagement with the second arcuate member 216. As will be apparent, the movement of the locking pin 228 is limited by the engagement of the stud 248 with the opposite ends of the slot 246.

If it is desired to be able to snap the second arcuate member 216 shut in the closed position without recourse to the stud 248 then this may be achieved by appropriate shaping of the head of the locking pin 226 and/or by providing the end 222 of the second arcuate member with a beveled surface 250. In this way as the beveled surface 250 comes into contact with the head of the locking pin 226 it pushes the locking pin 228 into the handle 204 against the action of the spring 240 until such time as the bore 224 is brought into alignment with the stepped bore 234.

In use, the head centering jig of the second embodiment is employed in the same manner as that of the first embodiment to identify a point on the femoral head in alignment with the central axis of the femoral neck. To this end the locating tool 202 is offered up to the femur with the second arcuate member 216 in the open position. Once the arcuate surface 210 of the first arcuate member 208 has been placed up against the femoral neck, the second arcuate member 216 is pivoted about hinge axis 220 to the closed position to encircle the femoral neck. The second arcuate member 216 is retained in the closed position with respect to the first arcuate member 208 by the receipt of the head 226 of the locking pin 228 within the bore 224.

Thereafter, as with the head centering jig of the first embodiment, the plane defined by the locating tool 202 is tilted by raising and lowering the handle 204 until such time as the first alignment rod 114 is aligned parallel to the central axis of the femoral neck when viewed anteriorly. Assuming that the appropriately sized jig has been selected and that the femoral neck is a close fit within the closed circle defined by arcuate surfaces 210 and 218, the central axis 136 of the guide tube 128 will lie within a plane parallel to the coronal plane. By then aligning the first alignment rod 144, the central axis 136 is brought into coincidence with the central axis of the femoral neck. If additional alignment is required a second alignment rod 148 may be aligned with the central axis of the femoral neck when viewed laterally. Once the surgeon is satisfied that the central axis 136 of the guide tube 128 is aligned with the central axis of the femoral neck he may use his free hand to drill the long pin through the guide tube 128 and into the femoral head. The head centering jig 200 is then disassembled and removed as previously described before performing the remaining steps of the Hip Resurfacing procedure.

Figure 19:
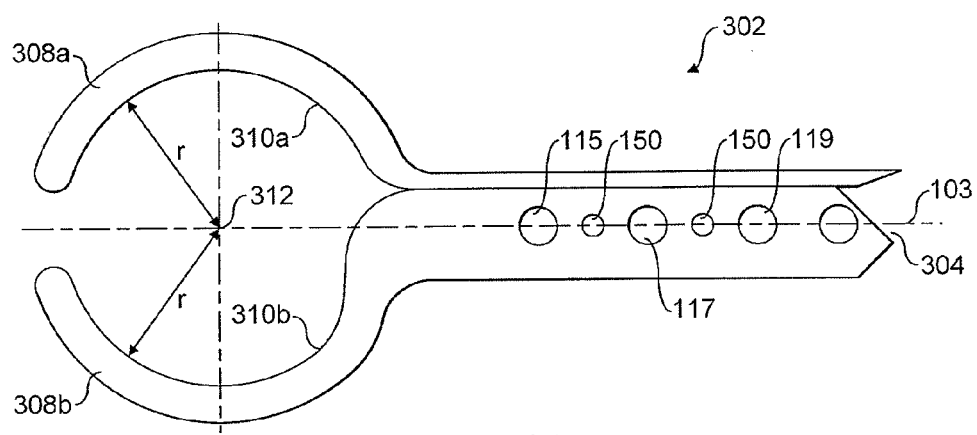
FIG. 19 is a plan view of a locating tool comprising two arms used in a third embodiment of the present invention in a closed position.
Figure 20:
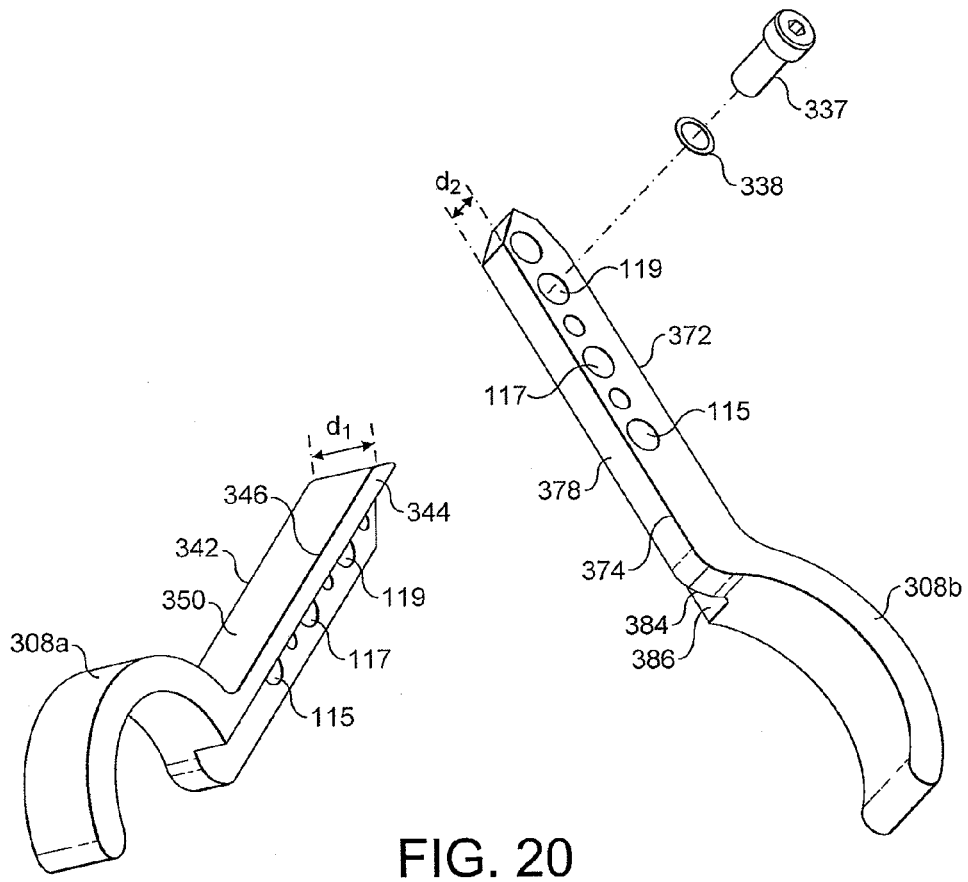
FIG. 20 is an exploded perspective view of the locating tool of FIG. 19.
Figure 21:
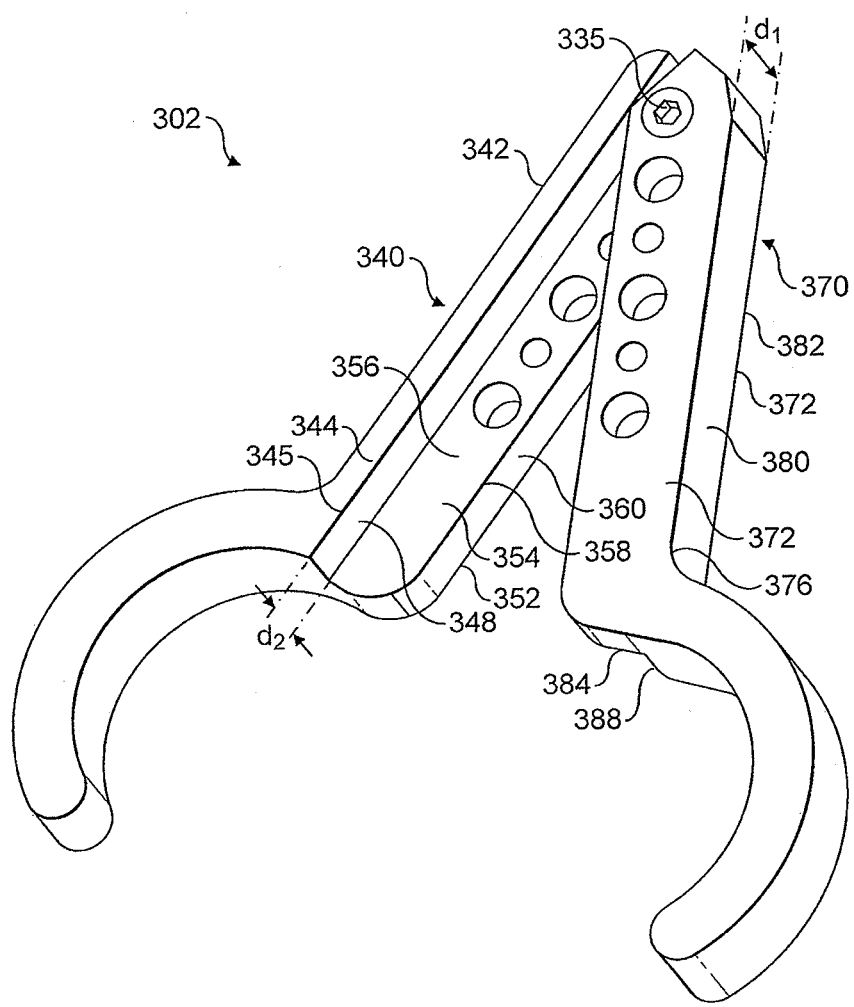
FIG. 21 is a perspective view of the locating tool of FIGS. 19 and 20 in an open position.

A locating tool 302 according to a third embodiment of the present invention is shown in FIGS. 19 to 21. The locating tool 302 is configured to be used with a retaining member 114, guide tube 128 and two alignment rods 144 and 148 as described in relation to the first embodiment and these features will not be described in detail in relation to the third embodiment.

As shown in FIG. 19, like the first and second embodiments, the locating tool 302 comprises an elongate handle 304. However, the locating tool 302 of the third embodiment differs from that of the first and second embodiments. In particular the locating tool 302 comprises a first arm 340 and a second arm 370, as shown in FIGS. 20 and 21. The first and second arms 340 and 370 comprise respective first and second elongate handles 342 and 372 which are designed to interlink to form the elongate handle 304. Each of the first and second elongate handles 342 and 372 are provided with apertures 115 and 119 for the receipt of the projecting studs 118 and 120 provided on the under surface of the retaining member 114. The first and second elongate handles 342 and 372 may also comprise the aperture 117 for use in securing the retaining member 114 to the handle 304 by means of a locating screw 116 as previously described. Alternatively, a locking screw 201 similar to that described in relation to FIG. 18 may be used for the securement of the retaining member 114 to the handle 304.

In any event the apertures 115, 117 (if present) and 119 are designed such that when the first and second elongate handles 342 and 372 are interlinked the apertures are mutually aligned.

The first and second arms 340 and 370 are hingedly attached by means of a hinge 335 at a proximal end of the elongate handle 304 as shown in FIG. 21. However, it will be appreciated that such an attachment is not an essential feature of the invention. The hinge 335 preferably comprises a pin 337 and a nut 338 as shown in FIG. 20.

As shown in FIGS. 20 and 21, the first elongate handle 342 comprises a first surface 345 which merges at inner and outer edges 344 and 346 with inner and outer downwardly depending side walls 348 and 350, respectively. The outer side wall 350 in turn merges with a second surface 352 at a distance d1 from the first surface 344, which is shown as being parallel to said first surface 344, although it will be understood that such a parallel arrangement is not an essential feature of the invention. By contrast, the inner side wall 348 merges with an inwardly extending third surface 354 at a distance d2, d2 being less than the distance d1, to form a step 356. Again, although the third surface 354 is depicted as being substantially parallel to the first and second surfaces 344 and 352 the invention is not so limited. The third surface 354 terminates at an inner edge 358 at a lower inner downwardly depending side wall 360 which in turn terminates with the second surface 352.

In contrast to the first elongate handle 342, the second elongate handle 370 comprises a first surface 372 which merges at inner and outer edges 374 and 376 with inner and outer downwardly depending side walls 378 and 380, respectively. The outer side wall 380 in turn merges with a second surface 382 at distance d1, from the first surface 372. By contrast, the inner side wall 378 merges with an outwardly extending third surface 384 at distance d2 which in turn merges with a lower inner downwardly depending wall 386 which merges with the second surface 382. The lower inner wall 386 and third surface 384 form a step 388. As previously discussed in relation to the first elongate handle 342, the first, second and third surfaces 372, 382 and 384 need not be in a parallel arrangement.

At a distal end, the first and second elongate handles 342 and 372 merge with first and second arcuate members 308a and 308b which define first and second arcuate surfaces 310a and 310b having a radius of curvaturer. When the locating tool 302 is in the closed position, as shown in FIG. 19, the first and second arcuate surfaces 310a and 310b have a centre of curvature 312 coincident with the point at which the central axis 136 of the guide tube 128 intersects the plane defined by the locating tool 302 and which lies on the longitudinal axis 103.

At their proximal ends, the first and second handle 342 and 372 are designed with tapers to allow for the first and second arms 340 and 370 to rotate freely about the hinge 335.

The locating tool 302 is moveable between an open position, as shown in FIG. 21, and a closed position, as shown in FIG. 19. In the open position the first and second arcuate members 308a and 308b are sufficiently spaced apart to permit the receipt of the femoral neck. Once the locating tool 302 is in position it is closed and held in the closed position by the retaining member 114 which is mounted on the elongate handle 304. The locating tool 302 can be additionally held in a closed position by the provision of a suitable closure means (not shown) at an end of the first and second arcuate members 308a and 308b remote from the first and second elongate handles 342 and 372. Alternatively the locating tool 302 may be provided with arcuate members similar to the arcuate members 208 and 216 described in relation to the second embodiment.

As with the head centering jig of the first and second embodiments, in order to accommodate the range of femur sizes present in the population, it will be necessary, in accordance with the third embodiment, to provide a range of locating tools 302 which differ in terms of the radius of curvature r, and therefore the arcs subtended by the first and second arcuate member 308a and 308b in the closed position. The length of the arm 126 would also need to vary from jig to jig in order to maintain the relationship between the central axis 136 of the guide tube 128 and its point of intersection with the plane defined by the locating tool 302.

Once the locating tool 302 is retained in the closed position by the fixation of the retaining member 114 to the elongate handle 304, as with the head centering jig of the first or second embodiments, the plane defined by the locating tool 302 is tilted by raising and lowering the handle 304 until such time as the first alignment rod 144 is aligned parallel to the central axis of the femoral neck when viewed anteriorly. Assuming that the appropriately sized jig has been selected and that the femoral neck is a close fit within the substantially closed circle defined by arcuate surfaces 310a and 310b, the central axis 136 of the guide tube 128 will lie within a plane parallel to the coronal plane. By then aligning the first alignment rod 144, the central axis 136 is brought into coincidence with the central axis of the femoral neck. If additional alignment is required a second alignment rod 148 may be aligned with the central axis of the femoral neck when viewed laterally. Once the surgeon is satisfied that the central axis 136 of the guide tube 128 is aligned with the central axis of the femoral neck he may use his free hand to drill the long pin through the guide tube 128 and into the femoral head. The head centering jig 300 is then disassembled and removed as previously described before performing the remaining steps of the Hip Resurfacing procedure.

Thus it will be apparent that the present invention as herein described provides a head centering jig that is less bulky than those of the prior art and which can be manipulated using only one hand. It will also be apparent that the use of the head centering jig no longer necessitates the exposure of the mid-lateral cortex of the femur.

We claim as our invention:

1. A method of identifying a point on the femoral head in alignment with a central axis of the femoral neck, the method comprising the steps of:
providing a jig comprising a first member having a locating member for at least partially receiving the femoral neck, the locating member having a surface defining a plane substantially perpendicular to the central axis of the femoral neck, a guide member mounted in spaced relation with respect to the first member and defining a central axis at right-angles to the plane defined by the locating member, the central axis intersecting the plane at a location a predetermined distance from said locating member, and an elongate alignment member mounted with respect to the first member, the elongate alignment member being laterally offset from and extending parallel to the central axis of the guide member,
exposing the femoral head and neck;
offering up the first member to the femoral neck so that the femoral neck is at least partially received by said locating member;
aligning the elongate alignment member laterally offset and substantially parallel to the central axis of the femoral neck; and identifying an intersection point at which the central axis of the guide member intersects the femoral head as the point on the femoral head in alignment with the central axis of the femoral neck.

2. The method in accordance with claim 1, wherein a mid-lateral cortex of the femur is not exposed.

3. The method in accordance with claim 1, wherein the first member is offered up to the femoral neck and the elongate alignment member is aligned using only one hand.

4. The method in accordance with claim 1, wherein the first member is offered up to the femoral neck in a lateral approach.

5. The method in accordance with claim 1, wherein the step of offering up the first member to the femoral neck comprises substantially encircling the femoral neck.

6. The method in accordance with claim 1, wherein the step of aligning the elongate alignment member comprises aligning the elongate alignment member with a central axis of the femoral neck when viewed from two orthogonal directions.

7. The method in accordance with claim 1 and further comprising the step of drilling along the central axis of the guide member and into the femoral head.

8. The method in accordance with claim 1 and further comprising the step of disassembling the jig prior to removal from the femoral neck.

9. The method in accordance with claim 1, wherein the jig is provided as part of a kit comprising a plurality of jigs having differing dimensions, the method further comprising the step of selecting the appropriate jig for the size of femoral head to be surveyed.

10. A method of identifying a point on the femoral head in alignment with a central axis of the femoral neck comprising:
providing a jig having
a first member having a locating member, the locating member having a surface defining a plane, the locating member comprising confronting surfaces adapted to substantially encircle the femoral neck, said confronting surfaces comprising first and second parts coupled by a hinge, at least one of said first and second parts being movable between an open position in which first and second parts are separated by a distance sufficient to receive the femoral neck and a closed position in which the first and second parts define a wall adapted to substantially surround the femoral neck;

a guide member mounted in spaced relation with respect to the first member and defining a central axis at right-angles to the plane defined by the locating member, the central axis of the guide member intersecting the plane at a location a predetermined distance from said locating member; and an elongate alignment member mounted with respect to the first member, the alignment member being laterally offset from and extending parallel to the central axis of the guide member;

exposing the femoral head and neck;

offering up the first member having the first and second parts in an open position to the femoral neck so that the femoral neck is at least partially received by said locating member;

aligning the elongate alignment member laterally offset and substantially parallel to the central axis of the femoral neck; and identifying an intersection point at which the central axis of the guide member intersects the femoral head as the point on the femoral head in alignment with the central axis of the femoral neck.

11. The method in accordance with claim 10, wherein the guide member comprises a hollow tube and the central axis of the guide member comprises a central axis of the tube, and the identifying step includes identifying the intersection point through the hollow tube.

12. The method in accordance with claim 10 further including the step of selectively detaching the guide member from the first member.

13. The method in accordance with claim 10 further comprising the step of drilling along the central axis of the guide member and into the femoral head.

14. The method in accordance with claim 10 further comprising the step of disassembling the jig prior to removal from the femoral neck.

15. A method for identifying a point on a femoral head in alignment with a central axis of an associated femoral neck comprising:

a jig including
  a first member having a locating member including a surface disposed in a plane substantially at right-angles to the central axis of the femoral neck to at least partially receive the femoral neck;

a guide member mounted in spaced relation with respect to the first member and defining a central axis at right-angles to the plane defined by the locating member, the central axis of the guide member intersecting the plane at a location a predetermined distance from said locating member, said axis defined by the guide member being substantially coincident with the central axis of the received femoral neck; and an elongate alignment member mounted with respect to the first member, the alignment member being laterally offset from and extending parallel to the central axis of the guide member, said elongate alignment member comprising first and second rods mounted with respect to the first member and extending parallel to and laterally offset from the central axis of the guide member, the first rod being spaced from said axis in a direction orthogonal to that in which the second rod is spaced from said axis;

exposing the femoral head and neck;

offering up the locating member to the femoral neck so that the femoral neck is at least partially received by said locating member;

aligning the elongate alignment member substantially parallel to the central axis of the femoral neck; and identifying an intersection point at which the central axis of the guide member intersects the femoral head as the point on the femoral head in alignment with the central axis of the femoral neck.

16. The method in accordance with claim 15, wherein the guide member comprises a hollow tube and the central axis of the guide member comprises a central axis of the tube, and the identifying step includes identifying the intersection point through the hollow tube.

17. The method in accordance with claim 15, wherein the step of aligning the elongate alignment member comprises aligning the elongate alignment member with a central axis of the femoral neck when viewed from two orthogonal directions.

18. The method in accordance with claim 15 further comprising the step of drilling along the central axis of the guide member and into the femoral head.

19. The method in accordance with claim 15 further comprising the step of disassembling the jig prior to removal from the femoral neck.

* * * * *